United States Patent
Martini et al.

(10) Patent No.: US 9,727,792 B2
(45) Date of Patent: Aug. 8, 2017

(54) METHOD AND DEVICE FOR TRACKING-BASED VISIBILITY RANGE ESTIMATION

(71) Applicant: Robert Bosch GmbH, Stuttgart (DE)

(72) Inventors: Johannes Martini, Wiesbaden (DE); Ulrich Stopper, Gerlingen (DE); Stephan Lenor, Stuttgart (DE); Stefan Weber, Saratoga, CA (US)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 14/703,278

(22) Filed: May 4, 2015

(65) Prior Publication Data

US 2015/0317524 A1 Nov. 5, 2015

(30) Foreign Application Priority Data

May 2, 2014 (DE) .......................... 10 2014 208 272

(51) Int. Cl.
 *G06K 9/00* (2006.01)
 *G06K 9/46* (2006.01)
 *G06K 9/62* (2006.01)
 *B60W 40/02* (2006.01)
 *G01N 21/53* (2006.01)

(52) U.S. Cl.
 CPC ......... *G06K 9/00791* (2013.01); *B60W 40/02* (2013.01); *G01N 21/538* (2013.01); *G06K 9/4661* (2013.01); *G06K 9/6267* (2013.01)

(58) Field of Classification Search
 CPC .......................... G01N 21/538; G06K 9/00805
 See application file for complete search history.

(56) References Cited

U.S. PATENT DOCUMENTS

2004/0046866 A1* 3/2004 Pochmuller ......... B60R 16/0237
 348/135

FOREIGN PATENT DOCUMENTS

EP 1303768 3/1985
FR WO03069275 A1 * 8/2003 ............. G01N 21/53

OTHER PUBLICATIONS

Bobel, Volker, "Function Minimization," University of Hamburg, Mar. 2003, Deutsches Elektronen-Synchrotron (DESY).*
Regression analysis, Wikipedia, the free encyclopedia, May 1, 2013, https://en.wikipedia.org/w/index.php?title=Regression_analysis&oldid=553084781.*

* cited by examiner

*Primary Examiner* — Raphael Schwartz
(74) *Attorney, Agent, or Firm* — Norton Rose Fulbright US LLP; Gerard Messina

(57) ABSTRACT

A method is provided for tracking-based visibility range estimation for a vehicle, the method including a step of tracking an object detected in a first image at a first point in time and in a second image at a second point in time, a step of ascertaining a first object luminance of the object and a first distance to the object at the first point in time and also ascertaining a second object luminance of the object and a second distance to the object at the second point in time, and also a step of determining an atmospheric extinction coefficient using the first object luminance, the second object luminance, the first distance, and the second distance, the atmospheric extinction coefficient being in direct correlation to visibility range.

27 Claims, 3 Drawing Sheets

METHOD AND DEVICE FOR TRACKING-BASED VISIBILITY RANGE ESTIMATION

FIELD OF THE INVENTION

The present invention relates to a method for tracking-based visibility range estimation, for example for a vehicle, and a corresponding device for the tracking-based visibility range estimation, and also to a corresponding computer program.

BACKGROUND INFORMATION

Due to a rapid further development of sensors and systems, an increasingly accurate detection of the vehicle surroundings is made possible. Different driver assistance systems may thus support the human driver in his or her driving task, and/or assume parts of the tasks completely. Various active and passive sensors work with the aid of different electromagnetic spectral ranges. Depending on the spectral range, more or less strong damping and scattering effects may occur due to atmospheric phenomena (rain, fog, . . . ). For cameras (spectral range approximately in the range of the visible light), mainly fog may in this way result in visibility limitations.

European Patent No. 1303768 describes a method for visibility range determination. To determine the visibility range in particular of a driver in a vehicle, a contrast is measured from at least two measuring positions of a measuring device, the positions being spaced at different distances from the object, and the relation of the measured contrast values is converted into a visibility range based on the difference of the distances of the measuring positions from the object.

SUMMARY

Against this background, using the approach presented here, a method for tracking-based visibility range estimation for a vehicle, furthermore a device for the tracking-based visibility range estimation for a vehicle which uses this method, and finally a corresponding computer program are presented.

Knowledge of the instantaneous visibility range is advantageous for several systems in a vehicle. From an object luminance of an object in a plurality of measuring positions spaced at different distances from an image sensor characteristic may be ascertained, which has a correlation to the visibility range. The object luminance may here be obtained from images from an image detection system or from an image detection device. In variants of the presented method, the number of the examined objects, the number of the analyzed images, or underlying mathematical models may be varied or combined in order to design the method more robustly.

A method for tracking-based visibility range estimation is presented, the method including the following steps:

tracking an object depicted in a first image detected at a first point in time and in at least one second image detected at a second point in time;

ascertaining a first object luminance of the object and a first distance to the object at the first point in time and also ascertaining a second object luminance of the object and a second distance to the object at a second point in time; and determining an atmospheric extinction coefficient using the first object luminance, the second object luminance, the first distance, and the second distance, the atmospheric extinction coefficient being in direct correlation to the visibility range.

The visibility range may be the visibility range prevailing in the surroundings of an image detection device. The object may be located in the surroundings. An image may be understood as a depiction of the surroundings obtained using the image detection device. The object may thereby be depicted in an area of the image. The image may have different intensity data. The object luminance may be understood as intensity data of the object. The object luminance may be a function of an object light and scattered ambient light. Tracking the object may be understood as recognizing and marking or extraction of one and the same object depiction of the object in multiple camera images. A camera image may be understood as an image from an image detection device. The first image may be detected by a first image detection device and the second image may be detected by a second image detection device. The first point in time may be different from the second point in time. In particular, if the first point in time corresponds to the second point in time, then the first distance to the object may be different from the second distance to the object.

The method for tracking-based visibility range estimation may be used for or in a vehicle. The method for tracking-based visibility range estimation may be used independently of a vehicle in a mobile camera which, for example, moves in the surroundings. Thus, the method may be used for example by a pedestrian using a smartphone. The method may also be used with a plurality of cameras or image detection devices which are designed to capture an object from different distances. In particular, the object may be detected at points in time which are preferably close together. Alternatively, the method for the tracking-based visibility range estimation may be used with a stationary image detection device for objects moving past.

To describe the fog density, extinction coefficient $K=K_a+K_s$ [1/m] may be used, which is made up of scattering coefficient $K_s$ [1/m] and absorption coefficient $K_a$ [1/m]. The extinction coefficient K may be, for example, directly connected to the human perception using the definition of meteorological visibility range $d_{met}$ [m]:

$$d_{met} = -\frac{\log(0.05)}{K} \quad (1)$$

The meteorological visibility range results as the distance at which an object is still perceivable with 5% of its original contrast.

For different reasons it may be interesting to be able to estimate extinction coefficient K. For example, drivers may be warned when they are traveling at a velocity unsuited to the visibility range. The velocity may even be automatically adapted corresponding to the visibility range. Furthermore, the fog density is an interesting variable for sensors and systems which work in the spectral range which is strongly attenuated by fog, for example, camera or LIDAR. These sensors, like humans, may no longer make reliable statements above their meteorological range. For example, when no object is detected 75 m ahead in the case of a visibility range of 50 m, this does not mean that there is no object situated there. Different algorithmic parameters may be adapted to the visibility conditions. Another use may be the control of fog lights, which may be turned on during fog for higher comfort, or the control of the rear fog lights, which must or should be turned on at a visibility range of below 50 m due to regulatory requirements such as the StVo (German highway code, Straβenverkehrsordnung) or to increase safety.

A system is presented here, which may estimate extinction coefficient K, in particular during daylight, particularly rapidly, or real-time capably, from intensity data and distance data of a camera.

In the step of determining, extinction coefficient K may be determined using a one-dimensional equation. Extinction coefficient K may be determined using a model for light transmission by atmospheric aerosols. Advantageously, a one-dimensional equation and additionally or alternatively a model of horizontal view may enable a more rapid determination of extinction coefficient K. The model of horizontal view may be formulated as a one-dimensional equation.

In the step of determining, extinction coefficient K may be determined using an estimation method from the one-dimensional equation. This makes it possible to approximately and very rapidly determine extinction coefficient K. The estimation method may be carried out iteratively and approach determined extinction coefficient K to critical extinction coefficient K of an objective functional with each iteration. Advantageously, at least three iterations may be carried out. Advantageously, less than five iterations are sufficient in order to approach determined extinction coefficient K in a favorable tolerance range to critical extinction coefficient K of the objective functional. Critical extinction coefficient K may be different from a "true" extinction coefficient K of the surroundings, it being possible, however, for critical extinction coefficient K to represent a best possible estimation as a minimum of the objective functional.

Extinction coefficient K may be determined in the step of determining using an iterative Newton's method. Advantageously, a trivial method is used for the determination of extinction coefficient K. A real-time-capable determination of extinction coefficient K may thus take place.

In a step of detecting, the first image may be detected at the first point in time and the second image may be detected at the second point in time following the first point in time. The images may be detected using an image detection device. The images may represent an item from the surroundings of the image detection device as an object, the distance representing a distance between the image detection device and the item. The item may be located at the first point in time at a first measuring position with regard to the vehicle. The thing may be located at the second point in time at a second measuring position with regard to the vehicle. The second measuring position may have a smaller distance with regard to the vehicle or the image detection device as the first measuring position at the first point in time.

In the step of detecting, the first image may be detected at the first point in time and the second image at the second point in time, whereby the images may be detected in the step of detecting using multiple image detection devices. The distance may thereby represent a distance between the respective image detection device and the item In the step of tracking, at least one additional object may be tracked. In the process, in the step of ascertaining an additional first object luminance of the additional object and an additional distance to the at least one additional object at the first point in time and also an additional second object luminance of the additional object and an additional second distance to the at least one additional object at the second point in time may be ascertained. In the step of determining, atmospheric extinction coefficient K may be determined using the additional first object luminance, the additional second object luminance, the additional first distance, and the additional second distance, whereby the method may become more robust. The method may be advantageously expanded to a multiplicity of objects.

The object may be tracked in the step of tracking in at least a third image detected at a third point in time. In the step of ascertaining, a third object luminance of the object and a third distance to the object at the third point in time may be ascertained. In the step of determining, the atmospheric extinction coefficient K may be determined using the third object luminance and the third distance.

In particular, the object may be tracked in a plurality of sequential images. In the step of ascertaining, a plurality of object luminances of the object and a plurality of respectively assigned distances to the object at a plurality of corresponding points in time may be ascertained thereupon. This means, per image from the plurality of images, an object luminance and an assigned distance may be ascertained per object and provided as a pair of variables to the step of determining A point in time at which the image was detected may also be assigned to each pair of variables. A plurality may be understood, for example, as a number between 10 and 100. It may be advantageous to use at least 50 sequential images to track at least one object therein and to analyze using the steps of ascertaining and determining. The points in time which are assignable to the value pairs may be distributed over a limited time frame which is not too large. The time frame may include a few seconds or less than one second. Thus, the time frame may be, for example, 0.5 seconds, 1 second, 2 seconds, or 5 seconds. At the same time, the object may be observed by multiple cameras or image detection devices at the same point in time from different distances. The tracking may mean or include registering or locating corresponding object points. Thus, a robust method with a robust result may be created.

The approach presented here also provides a device which is designed for carrying out, controlling, or implementing the steps of one variant of a method provided here in appropriate devices. The object on which the present invention is based may also be achieved rapidly and efficiently by this embodiment variant of the present invention in the form of a device.

In the present case, a device may be understood to mean an electrical device which processes sensor signals and outputs control and/or data signals as a function thereof. The device may include an interface which may be designed as hardware and/or software. In a hardware design, the interfaces may, for example, be part of a so-called system ASIC, which includes various functions of the device. However, it is also possible that the interfaces are dedicated integrated circuits or are made, at least in part, of discrete components. In a software design, the interfaces may be software modules, which, for example, are present on a microcontroller together with other software modules.

Also advantageous is a computer program product or computer program including program code which may be stored on a machine-readable carrier or storage medium such as a semiconductor memory, a hard disk memory, or an optical memory, and used for carrying out, implementing, and/or controlling the steps of the method according to one of the above-described specific embodiments, in particular when the program product or program is executed on a computer or a device.

DETAILED DESCRIPTION

Figure 1:
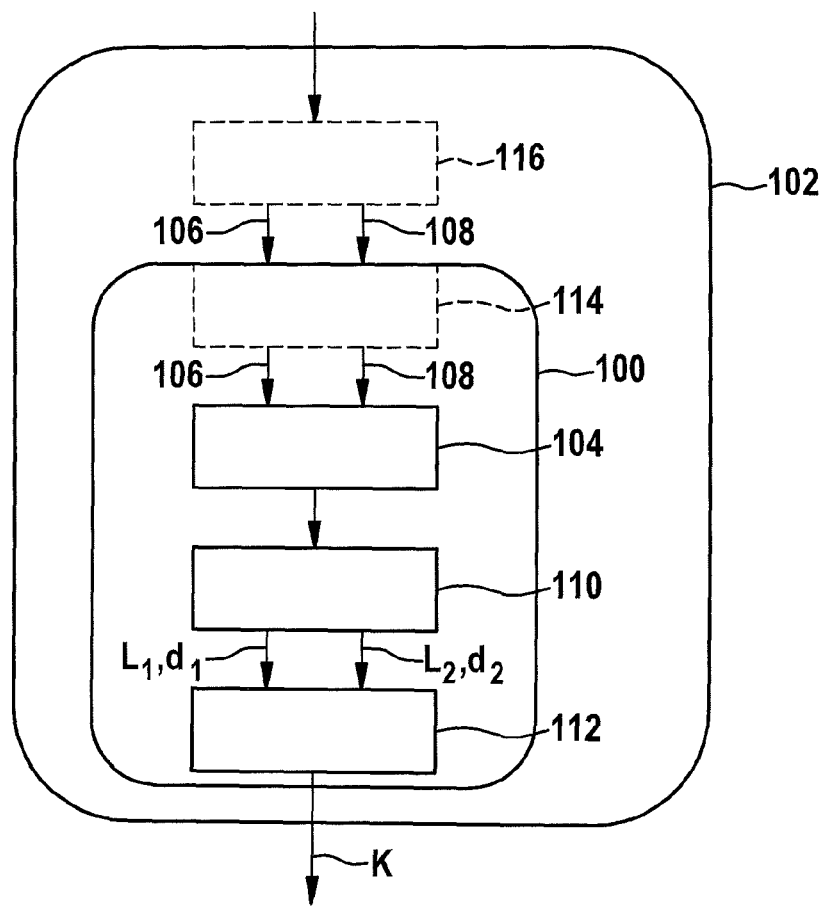
FIG. 1 shows a block diagram of a device for tracking-based visibility range estimation for a vehicle according to one exemplary embodiment of the present invention.

In the following description of advantageous exemplary embodiments of the present invention, identical or similar reference numerals are used for elements which are similar operating elements and represented in the various figures, a repeated description of these elements being omitted.

FIG. 1 shows a block diagram of a device 100 for tracking-based visibility range estimation for a vehicle 102 according to one exemplary embodiment of the present invention. Device 100 includes a tracking device 104 for tracking a depiction of an object in a first image 106 detected at a first point in time and in a second image 108 detected at a second point in time, an ascertainment device 110 for ascertaining a first object luminance $L_1$ of the object and a first distance $d_1$ to the object at the first point in time and also ascertaining a second object luminance $L_2$ of the object and a second distance $d_2$ to the object at the second point in time, and also a determination device 112 for determining an atmospheric extinction coefficient K using first object luminance $L_1$, second object luminance $L_2$, first distance $d_1$, and second distance $d_2$, atmospheric extinction coefficient K being directly correlated to visibility range $d_{met}$. The correlation between atmospheric extinction coefficient K and visibility range $d_{met}$ is represented in equation (1). The first point in time is thereby chronologically prior to the second point in time.

Furthermore, in the exemplary embodiment shown in FIG. 1, device 100 has an interface 114 for detecting first image 106 at the first point in time and second image 108 at the second point in time following the first point in time. Images 106, 108 are detected using an image detection device 116. Images 106, 108 represent an object, for example an item from the surroundings of image detection device 116, distances $d_1$, $d_2$ each representing a distance between image detection device 116 and the item.

Figure 2:
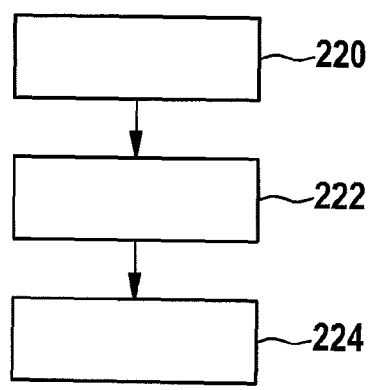
FIG. 2 shows a flow chart of a method for tracking-based visibility range estimation according to one exemplary embodiment of the present invention.

FIG. 2 shows a flow chart of a method for tracking-based visibility range estimation according to one exemplary embodiment of the present invention. The method includes a step 220 of tracking an object, a step 222 of ascertaining, and a step 224 of determining an atmospheric extinction coefficient K. In step 220 of tracking, a depiction of an object is tracked in a first image detected at a first point in time and in a second image detected at a second point in time. The object is thus recognized and a position and extent of the depiction of the object in the image is ascertained in the image in order to be able to further examine the area according to the depiction of the object in the following steps. In step 222 of ascertaining, an object luminance and a distance value are ascertained for the object and provided as a pair of variables. Thus, a first object luminance of the object is ascertained in the image recorded at the first point in time and a second object luminance of the object is ascertained in the image recorded at the second point in time, for example by using the respective images. The assignable first distance and second distance between the object and an image detection device are ascertained, depending on the exemplary embodiment, from the image, from additional data from the image detection device, or from another sensor. In step 224 of determining, atmospheric extinction coefficient K is determined using the first object luminance, the second object luminance, the first distance, and the second distance, the atmospheric extinction coefficient being directly correlated to the visibility range. The correlation between atmospheric extinction coefficient K and visibility range $d_{met}$ is represented in equation (1).

In one exemplary embodiment, in step 224 of determining, extinction coefficient K is determined using a one-dimensional equation and additionally or alternatively a model of horizontal view.

In one exemplary embodiment, extinction coefficient K is determined in step 224 of determining using an estimation method from the one-dimensional equation.

In one exemplary embodiment, extinction coefficient K is determined in step 224 of determining using an iterative Newton's method.

In one exemplary embodiment, the method includes an optional step of detecting the first image at the first point in time and the second image at the second point in time following the first point in time. In the step of detecting, the images are detected using an image detection device, the images representing an item from the surroundings of the image detection device as an object, the distance representing a distance between the image detection device and the item In one exemplary embodiment, at least one additional object is tracked in step 220 of tracking. Then in step 222 of ascertaining, an additional first object luminance of the additional object and an additional first distance to the at least one additional object at the first point in time is ascertained and also an additional second object luminance of the additional object and an additional second distance to the at least one additional object at the second point in time is ascertained. In step 224 of determining, the atmospheric extinction coefficient is determined using the additional first object luminance, the additional second object luminance, the additional first distance, and the additional second distance.

In one exemplary embodiment, a depiction of the object is tracked in step 220 of tracking in a third image detected at a third point in time, whereby in step 222 of ascertaining, a third object luminance of the object and a third distance to the object at the third point in time is ascertained, and in step 224 of determining, the atmospheric extinction coefficient being determined using the third object luminance and the third distance.

In one exemplary embodiment, additional pieces of surroundings information (for example surroundings luminance, object knowledge, . . . ) are also incorporated into step 224 of determining. These may be obtained from the image and/or from additional sensors and/or from the context, among others.

Figure 3:
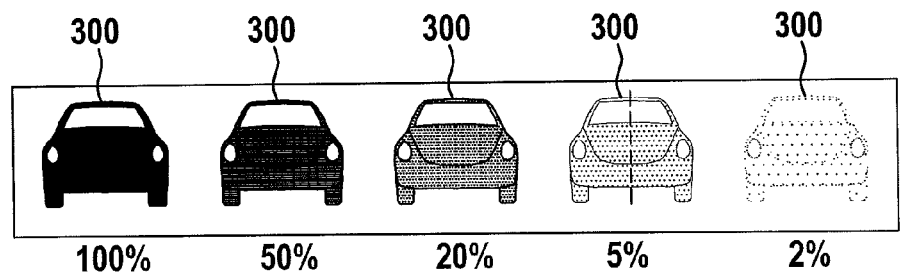
FIG. 3 shows a schematic representation of a meteorological visibility range according to one exemplary embodiment of the present invention.

FIG. 3 shows a schematic representation of a meteorological visibility range $d_{met}$ according to one exemplary embodiment of the present invention. Meteorological visibility range $d_{met}$ results from the distance at which an object is still perceivable with 5% of its original contrast. FIG. 3 thus shows a silhouette of a vehicle in five views next to one another, the contrast varying, from an original contrast referred to as 100% to a contrast referred to as 2%. Between them, the silhouette is shown with 50%, 20% and 5%. The threshold of perception lies at a contrast of 5%.

Figure 4:
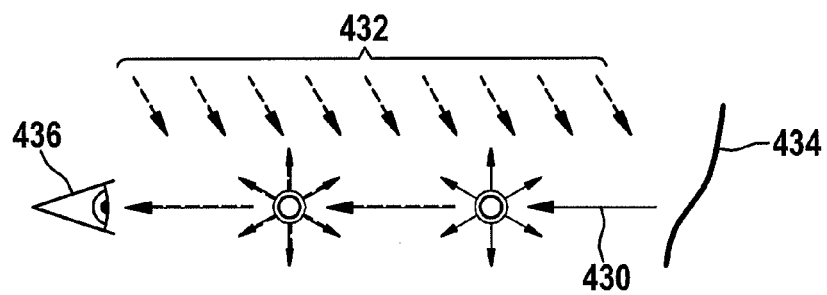
FIG. 4 shows a schematic representation of a relationship of object light and scattered ambient light according to one exemplary embodiment of the present invention.

FIG. 4 shows a schematic representation of a correlation between object light 430 and ambient light 432 scattered in according to one exemplary embodiment of the present invention. Object light 430 is attenuated on the path from object 434, for example an item, to viewer 436 and enhanced by ambient light 432 scattered in.

The approach described here is based on the tracking of objects, parts of surfaces or points across two or more frames or images of a camera. When these tracked entities—here denoted with reference numeral 434—are moved in their distance relative to the camera, the luminance or object luminance is modified by the fog Luminance here is to mean not only the classic photometric luminance. Here, the term is to represent any arbitrary (but over the course of the embodiments constant) spectral weighting of radiation density Luminance may here in particular also represent the spectral weighting according to the sensitivity curve of individual pixels of the camera imager or of the image detection device.

This correlation between luminance and object distance is described in more detail by Koschmieder's model of horizontal visual range, for example:

$$L = e^{-Kd}L_0 + (1 - e^{-Kd})L_{air} \qquad (2)$$

parameters $L_0$ and $L_{air}$ representing the luminance of the object and the ambient light, and d [m] representing the distance between object and viewer. L is the object light perceived by the viewer, which is composed according to equation (2) of attenuated object light $L_0$ and ambient light $L_{air}$ scattered in.

According to one exemplary embodiment, when a road sign is tracked during passing by a front camera during fog, the luminance (perceived lightness) decreases when approaching the road sign since less ambient light is scattered into the optical path and the light reflected by the object is weaker than the ambient light. Therefore, a curve of decreasing luminances results during tracking. If the distances to the tracked object are measured simultaneously, the luminance curve may also be plotted over the distance. The distances or spaces to the tracked object may, for example, be measured and determined via "structure from motion" in a mono camera, via stereo vision or via other sensors, for example, LIDAR. One example for a luminance curve over the distance or the space is shown in FIG. 5.

The distances may also be smoothed, interpolated and extrapolated during the process in order to also obtain distances in areas of the track at which a distance estimation is difficult or impossible, but the object may already be tracked. Information about the distance traveled between the recording points in time (for example, using ESP, GPS, ego-motion estimation, . . . ) may be taken into account during the process.

Figure 5:
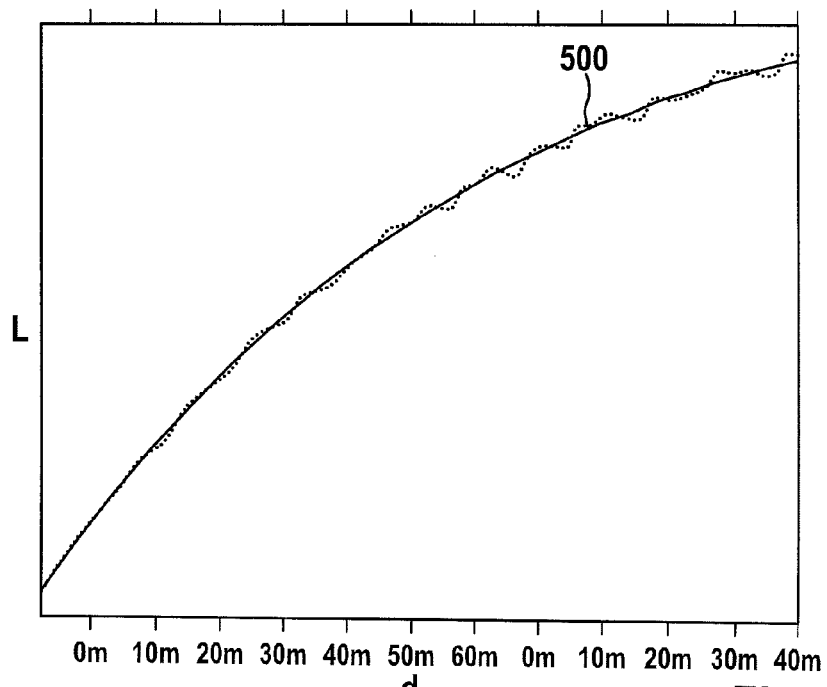
FIG. 5 shows a representation of measured luminances plotted over a distance according to one exemplary embodiment of the present invention.

FIG. 5 shows a representation of measured luminances plotted over a space according to one exemplary embodiment of the present invention. In a Cartesian coordinate system, a distance d is plotted on the abscissa and a luminance L of an object is plotted on the ordinate. Actual measuring points are plotted as dots, i.e., measured luminances of a tracked object are plotted over the space. As a continuous line, an adjusted model curve is represented according to Koschmieder's model of horizontal visual range, corresponding to Equation (2).

Figure 6:
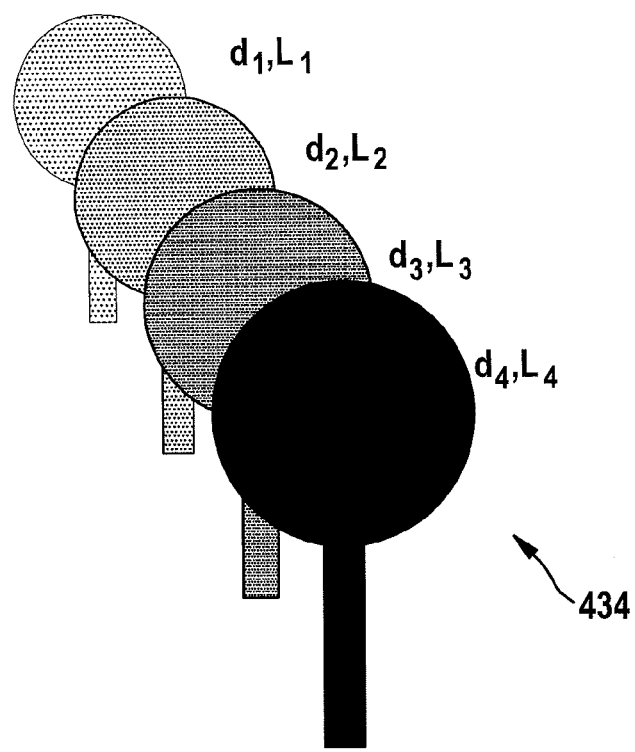
FIG. 6 shows a schematic representation of an object at different distances according to one exemplary embodiment of the present invention.

FIG. 6 shows a schematic representation of an object 434 at different distances according to one exemplary embodiment of the present invention. The luminances of an object are detected at different distances. The object represented in an image may be understood, for example, as a depiction of a real item. The luminance is referred to as L, the space or the distance as d. The indices refer to the point in time; $L_1$ represents the luminance at a first point in time, $L_2$ represents the luminance at a second point in time. An image is assigned to each point in time.

Thus the value pairs $(L_1; d_1), \ldots, (L_N; d_N)$ result in an object, N being the number of the frames or images in which the object was able to be tracked. In order to make an inference using Koschmieder's model according to equation (2) or also other models regarding the underlying extinction coefficient K, it is recommended that the value pairs preferably correspond to the predefined model; for Koschmieder:

$$L_1 = e^{-Kd_1}L_0 + (1 - e^{-Kd_1})L_{air}, \qquad (3)$$

$$\vdots$$

$$L_N = e^{-Kd_N}L_0 + (1 - e^{-Kd_N})L_{air}.$$

Since equation system (3) for N>3 based on noisy real data generally cannot be solved accurately, the parameters $(K; L_0; L_{air})$ are estimated in such a way that equations (3) within the sense of the least error squares are fulfilled as best possible:

$$\sum_{n=1}^{N} ([e^{-Kd_n}L_0 + (1 - e^{-Kd_n})L_{air}] - L_n)^2 \to \min$$

Extinction coefficient K, in particular, also meteorological visibility range $d_{met}$, may thus be estimated from image sequences.

Figure 7:
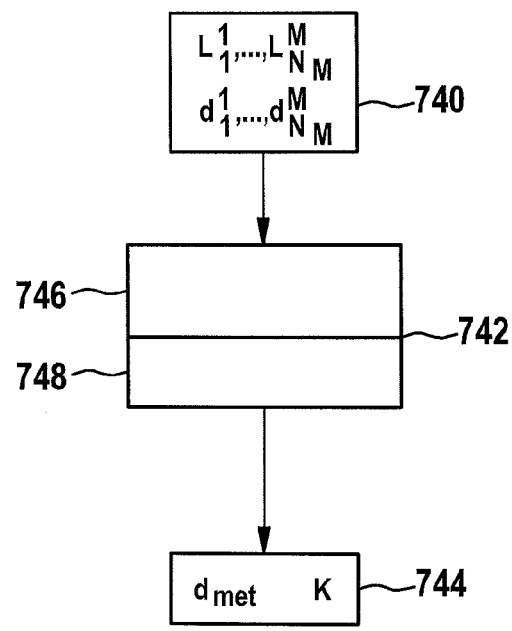
FIG. 7 shows a block diagram of a signal curve according to one exemplary embodiment of the present invention.

FIG. 7 shows a block diagram of a signal curve according to one exemplary embodiment of the present invention. In a first block 740, the signals to be processed are read in or recorded, in a second block 742, the signals to be processed are processed, and in third block 744, a visibility range signal $d_{met}$ or an extinction coefficient signal K is provided. Block 742 includes two sub blocks 746, 748.

In block 740, the value pairs $(L_1; d_1), \ldots, (L_N; d_N)$ are read in or recorded for one or a plurality of object(s). In first sub block 746 of block 742, a model fit for estimating extinction coefficient K is carried out, and second sub block 748 of block 742 provides means suitable for this purpose.

First sub block 746 represents a system which uses measuring data across tracked object luminances and distances via a model for estimating atmospheric extinction coefficient K or other fog properties.

Second sub block 748 represents the system, which uses a subsequently described method for minimizing the concrete Koschmieder's model functional (which may be used in first sub block 746), and thus becomes real-time capable.

Advantages of the general approach in first sub block 746 are that, due to its novelty, it is able to estimate extinction coefficients K or visibility range $d_{met}$ independently of previously existing methods, and thus may be used alone or in combination (for validation). It is independent of a road traffic scenario and could be used in principle in every system which estimates luminances and associated distances.

A further advantage is the ease of integrability into an existing system. Thus, arbitrarily tracked objects, street signs, tracked rivers, etc. might be incorporated without additional complexity for visibility range estimation. The actually very expensive estimation in first sub block 746 (minimization of a complex functional into ≥3 parameters) becomes very cost-efficient due to second sub block 748.

First sub block 746 is described in the following in greater detail. Defined should be object luminances (or almost-linear representations of object luminances) $L_1^1, \ldots, L_{N_1}^1, \ldots, L_1^M, \ldots, L_{N_M}^M$ of M≥1 object(s) and associated distances $d_1^1, \ldots, d_{N_1}^1, \ldots, d_1^M, \ldots, d_{N_M}^M$, where Nm=length of the object track m, for all m ∈ {1, . . . , M}. A model-based estimation of extinction coefficient K is carried out based on these data. For the Koschmieder Model from equation 2, this means that equation system:

$$\text{obj. 1:} \begin{cases} L_1^1 = L_{air} + (L_0^1 - L_{air})e^{-Kd_1^1} \\ \vdots \\ L_{N_1}^1 = L_{air} + (L_0^1 - L_{air})e^{-Kd_{N_1}^1} \end{cases} \quad (5)$$

$$\vdots$$

$$\text{obj. M:} \begin{cases} L_1^M = L_{air} + (L_0^M - L_{air})e^{-Kd_1^M} \\ \vdots \\ L_{N_M}^M = L_{air} + (L_0^M - L_{air})e^{-Kd_{N_M}^M} \end{cases}$$

may be solved optimally in model parameters K, $L_{air}$, $L_0^1, \ldots, L_0^M$, in that functional $\mathcal{F}$ is minimized.

$$\mathcal{F}: (K, L_{air}, L_0^1, \ldots, L_0^M) \mapsto \quad (6)$$

$$\sum_{m=1}^{M} \sum_{n=1}^{N_m} \left( \left[ e^{-Kd_n^m} L_0^m + (1 - e^{-Kd_n^m}) L_{air} \right] - L_n^m \right)^2$$

Since each object has its own intrinsic luminance $L_0$, an additional parameter is added per object, resulting in a total of M+2 parameters.

Alternatively, the model may also be very simple, roughly, "objects which move toward me become darker, which is indicative of fog". Even trained fog recognition algorithms or machine learning algorithms, which specifically determine a trained visibility range, could be constructed on observations of this type.

In one exemplary embodiment, measuring uncertainties may be incorporated into the functional and thus into the parameter estimation. For measuring uncertainties, which are expressed as standard deviations $\sigma_n^m$ in the measurements $L_n^m$, the following maximum likelihood target functional results from underlying normally distributed random process:

$$\mathcal{F}: (K, L_{air}, L_0^1, \ldots, L_0^M) \mapsto \quad (7)$$

$$\sum_{m=1}^{M} \sum_{n=1}^{N_m} \frac{1}{(\sigma_n^m)^2} \left( \left[ e^{-Kd_n^m} L_0^m + (1 - e^{-Kd_n^m}) L_{air} \right] - L_n^m \right)^2$$

Second sub block 748 is described in greater detail in the following. A large expense is necessary (depending on the number M of objects and the length of object tracks $N_m$) in order to be able to minimize functional $\mathcal{F}$ with the aid of conventional methods (gradient descent, Newton's method, Levenberg-Marquardt, . . . ). This minimization could only be integrated into a real-time system with difficulty and would demand many resources there. In this exemplary embodiment, a system is described which, instead of a minimization of functional, carries out an equivalent resolution of a one-dimensional equation f(K)=0. According to the expense for calculating the one-dimensional equation f(K), this is a much more cost-efficient problem. For example, the iterative Newton's method, K:=K−f(K)/f'(K), may be used for the resolution of f(K)=0. For one-dimensional equation f presented below, few (precisely 3) iterations suffice with starting value K:=0 for a sufficient precision of all forms of (simulated) data sets.

A one-dimensional equation f which meets the required property may be calculated as follows:

$$f(K) = L_{air}^2 (S_{eed} - S_{ed}) + L_{air} \left( \sum_{m=1}^{M} L_0^m S_{ed}^m - 2 \sum_{m=1}^{M} L_0^m S_{eed}^m + S_{Led} \right) + \quad (8)$$

$$\sum_{m=1}^{M} L_0^m L_0^m S_{eed}^m - \sum_{m=1}^{M} L_0^m S_{Led}^m,$$

where $$\forall j \in \{1, \ldots, M\}: L_0^j = \frac{S_{Le}^j + L_{air}(S_{ee}^j - S_e^j)}{S_{ee}^j}, \text{ and} \quad (9)$$

$$L_{air} = \frac{S_L - \sum_{m=1}^{M} \frac{S_e^m S_{Le}^m}{S_{ee}^m}}{S_1 - \sum_{m=1}^{M} \frac{S_e^m S_e^m}{S_{ee}^m}}, \quad (10)$$

and also an abbreviated notation is used:

$$S_1^j := \sum_{n=1}^{N_j} 1, \quad (11)$$

$$S_e^j := \sum_{n=1}^{N_j} e^{-Kd_n^j},$$

$$S_{ee}^j := \sum_{n=1}^{N_j} e^{-Kd_n^j} e^{-Kd_n^j},$$

$$S_L^j := \sum_{n=1}^{N_j} L_n^j,$$

$$S_{Le}^j := \sum_{n=1}^{N_j} L_n^j e^{-Kd_n^j},$$

$$S_{ed}^j := \sum_{n=1}^{N_j} d_n^j e^{-Kd_n^j},$$

$$S_{eed}^j := \sum_{n=1}^{N_j} d_n^j e^{-Kd_n^j} e^{-Kd_n^j},$$

$$S^* := \sum_{m=1}^{M} S^m_*.$$

The derivation of the one-dimensional equation f according to extinction coefficient K (required for Newton's Method) is moreover trivially determinable.

Since the determination of the luminance from the image intensity is only possible using exact radiometric or photometric calibration of the camera, luminance L may here also represent a (approximately) linear representation of the luminance, i.e., L=α·luminance+β.

Saturation and quantification effects, as well as other inaccuracies in the linear camera model represent no problem. This is since, on the one hand, a linearly transformed representation of the luminance represents no problem for the estimation of extinction coefficient K using the above-mentioned method. And, on the other hand, the relatively small inaccuracies due to quantification and similar effects due to the estimation do not result in any important distortion of the result per error square. A saturation may furthermore be detected and saturated measured luminances may be ignored during the extinction coefficient estimation or K estimation.

Further embodiment variants: In order to improve the estimation of extinction coefficient K with the aid of a model, it may be useful to limit the other model parameters by other measurements. This may be implemented by fixing the parameter (it is then no longer estimated), constraints on the parameter (it is only exactly estimated within the constraints), or by an additional penalty term (deviations of the parameter from the specification are penalized).

For example, the parameter for the luminance of the ambient light $L_{air}$ in the model could also be estimated independently from the image according to equation (2) (is useful, for the luminance of the ambient light $L_{air}$ to observe the luminances of the visible horizon and for example to average them). Now, functional F may be minimized by maintaining the luminance of ambient light $L_{air}$ or using constrained luminance of ambient light $L_{air}$. If the uncertainty of the estimation of the luminance of the ambient light, in short, the $L_{air}$ estimate, is known, a weighted penalty term may be added to functional F, for example, for estimated $\hat{L}_{air}$ and λ, which describes the reliability of the estimation:

$$\mathcal{F}_{\lambda,\hat{L}_{air}}:(K,L_{air},L_0^1,\ldots L_0^M) \mapsto$$
$$\mathcal{F}(K,L_{air},L_0^1,\ldots L_0^M)+\lambda(L_{air}-\hat{L}_{air})^2 \qquad (12)$$

In this variant as well, a $f_{\lambda,\hat{L}_{air}}$ may be found in such a way that exactly $f_{\lambda,\hat{L}_{air}}(K)=0$ in case the other parameters may be found in such a way, such that $\mathcal{F}_{\lambda,\hat{L}_{air}}$ is minimized in this parameter selection.

The step carried out in second sub block 748 thereby appears advantageous for the implementation of (A) (=minimization of F) in a real-time system.

The exemplary embodiments described here and illustrated in the figures are selected only as examples. Different exemplary embodiments may be combined with each other completely or in regard to individual features. One exemplary embodiment may also be supplemented by features of another exemplary embodiment.

Furthermore, the method steps presented here may also be repeated or carried out in a sequence different from the sequence described.

If one exemplary embodiment includes an "and/or" link between a first feature and a second feature, this should be read in such a way that the exemplary embodiment according to one specific embodiment includes both the first feature and the second feature, and according to an additional specific embodiment includes either only the first feature or only the second feature.

What is claimed is:

1. A method for supporting safe driving of a vehicle, the method comprising:
    tracking, by a driver assistance system of the vehicle, an object depicted in a first image detected at a first point in time and in at least one second image detected at a second point in time;
    ascertaining, by the driver assistance system, a first object luminance of the object and a first distance to the object at the first point in time;
    ascertaining, by the driver assistance system, a second object luminance of the object and a second distance to the object at the second point in time; and
    determining, by the driver assistance system, an atmospheric extinction coefficient using the first object luminance, the second object luminance, the first distance, and the second distance, the atmospheric extinction coefficient being in direct correlation to a visibility range;
    estimating, by the driver assistance system, the visibility range using the determined atmospheric extinction coefficient; and
    warning a driver or adapting a driving of the vehicle, by the driver assistance system, based on the estimated visibility range;
    wherein the atmospheric extinction coefficient is determined using a one-dimensional equation of:

$$F(K) = L_{air}^2(S_{eed} - S_{ed}) +$$
$$L_{air}\left(\sum_{m=1}^{M} L_0^m S_{ed}^m - 2\sum_{m=1}^{M} L_0^m S_{eed}^m + S_{Led}\right) + \sum_{m=1}^{M} L_0^m L_0^m S_{eed}^m - \sum_{m=1}^{M} L_0^m S_{Led}^m.$$

2. A method for supporting safe driving of a vehicle, the method comprising:
    tracking, by a driver assistance system of the vehicle, an object depicted in a first image detected at a first point in time and in at least one second image detected at a second point in time;
    ascertaining, by the driver assistance system, a value of a first overall luminance corresponding to the object and a value of a first distance to the object at the first point in time;
    ascertaining, by the driver assistance system, a value of a second overall luminance corresponding to the object and a value of a second distance to the object at the second point in time;
    fitting, by regression, the value of the first overall luminance, the value of the second overall luminance, the value of the first distance, and the value of the second distance to a model that models overall luminance against parameters that include an air luminance, a luminance of the object, object distance, and an atmospheric extinction coefficient, thereby obtaining an estimate of the air luminance, the luminance of the object, and the atmospheric extinction coefficient;
    estimating, by the driver assistance system, the visibility range using the estimated atmospheric extinction coefficient; and warning a driver or adapting a driving of the vehicle, by the driver assistance system, based on the estimated visibility range.

3. The method as recited in claim 1, wherein the atmospheric extinction coefficient is determined using an estimation method from the one-dimensional equation.

4. The method as recited in claim 1, wherein the atmospheric extinction coefficient is determined using an iterative Newton's method.

5. The method as recited in claim 1, further comprising:
detecting the first image at the first point in time and the second image at a second point in time following the first point in time, wherein:
in the step of detecting, the first and second images are detected using at least one image detection device,
the first and second images represent an item as the object from surroundings of the at least one image detection device, and
a distance is present between the at least one image detection device and the item.

6. The method as recited in claim 1, wherein:
at least one additional object is tracked,
an additional first object luminance of the additional object is ascertained,
an additional first distance to the at least one additional object at the first point in time is ascertained,
an additional second object luminance of the additional object is ascertained,
an additional second distance to the at least one additional object at the second point in time is ascertained, and
in the step of determining, the atmospheric extinction coefficient is determined using the additional first object luminance, the additional second object luminance, the additional first distance, and the additional second distance.

7. The method as recited in claim 1, wherein:
the object is tracked in at least a third image detected at a third point in time,
a third object luminance of the object is ascertained,
a third distance to the object at the third point in time is ascertained, and
the atmospheric extinction coefficient is determined using the third object luminance and the third distance.

8. A device for supporting safe driving of a vehicle, the device comprising:
a processing circuitry that is configured for:
tracking an object depicted in a first image detected at a first point in time and in at least one second image detected at a second point in time;
ascertaining a first object luminance of the object and a first distance to the object at the first point in time;
ascertaining a second object luminance of the object and a second distance to the object at the second point in time;
determining an atmospheric extinction coefficient using the first object luminance, the second object luminance, the first distance, and the second distance, the atmospheric extinction coefficient being in direct correlation to a visibility range;
estimating the visibility range using the determined atmospheric extinction coefficient; and
warning a driver or adapting a driving of the vehicle based on the estimated visibility range;
wherein the atmospheric extinction coefficient is determined using a one-dimensional equation of:

$$F(K) = L_{air}^2(S_{eed} - S_{ed}) + L_{air}\left(\sum_{m=1}^{M} L_0^m S_{ed}^m - 2\sum_{m=1}^{M} L_0^m S_{eed}^m + S_{Led}\right) + \sum_{m=1}^{M} L_0^m L_0^m S_{eed}^m - \sum_{m=1}^{M} L_0^m S_{Led}^m.$$

9. A non-transitory machine-readable memory medium having a computer program that is executable by a processor of a driver assistance system of a vehicle and that, when executed by the processor, causes the processor to carry out a method for supporting safe driving of the vehicle, the method comprising:
tracking an object depicted in a first image detected at a first point in time and in at least one second image detected at a second point in time;
ascertaining a first object luminance of the object and a first distance to the object at the first point in time;
ascertaining a second object luminance of the object and a second distance to the object at the second point in time;
determining an atmospheric extinction coefficient using the first object luminance, the second object luminance, the first distance, and the second distance, the atmospheric extinction coefficient being in direct correlation to a visibility range;
estimating the visibility range using the determined atmospheric extinction coefficient; and
warning a driver or adapting a driving of the vehicle based on the estimated visibility range;
wherein the atmospheric extinction coefficient is determined using a one-dimensional equation of:

$$F(K) = L_{air}^2(S_{eed} - S_{ed}) + L_{air}\left(\sum_{m=1}^{M} L_0^m S_{ed}^m - 2\sum_{m=1}^{M} L_0^m S_{eed}^m + S_{Led}\right) + \sum_{m=1}^{M} L_0^m L_0^m S_{eed}^m - \sum_{m=1}^{M} L_0^m S_{Led}^m.$$

10. The method as recited in claim 2, wherein the fitting using the regression additionally yields an estimate for the air luminance.

11. The method as recited in claim 2, wherein:
the model is $L_N = e^{-Kd_N}L_o + (1-e^{-Kd_N})L_{air}$ or its algebraic equivalent;
$L_N$ is the value of the overall luminance for point in time N;
$L_o$ is the value of the luminance for object o;
$L_{air}$ is the value of the air luminance;
$d_N$ is the value of the distance of the object for point in time N; and
K is the atmospheric extinction coefficient.

12. The method as recited in claim 11, wherein the fitting using the regression yields respective estimates for each of $L_o$ and $L_{air}$ by the fitting of each of the values of $d_N$ and $L_N$ of each of the first and second points in time to the model.

13. The method as recited in claim 2, wherein least squared error is used as the regression.

14. The method as recited in claim 2, wherein the model models light transmission by an atmospheric aerosol.

15. The method as recited in claim 2, wherein:
the regression includes a plurality of fitting iterations;
the model includes a first plurality of variables, the first plurality of variables including a first variable representing the first and second overall luminance and into which the values of the first overall luminance and the second overall luminance are plugged in each of the iterations, and a second variable representing the first and second distances and into which the values of the first and second distances are plugged in each of the iterations;

the model includes a second plurality of variables, the values of which are modified over the course of the plurality of fitting iterations; and the second plurality of variables includes a third variable representing the atmospheric extinction coefficient.

16. The method as recited in claim 15, wherein the second plurality of variables further include a fourth variable representing the air luminance and a fifth variable representing the luminance of the object.

17. The method as recited in claim 15, wherein:

the model is $L_N = e^{-Kd_N}L_o + (1-e^{-Kd_N})L_{air}$ or its algebraic equivalent;

$L_N$ is the first variable, into which are plugged values of the overall luminance per point in time N;

$L_{air}$ is a fourth variable representing an unknown value of the air luminance;

$L_o$ is a fifth variable representing the luminance for object o;

$d_N$ is the second variable, in which are plugged values of the distance of the object per point in time N; and K is the fourth variable representing the atmospheric extinction coefficient.

18. The method as recited in claim 17, wherein the fitting using the regression yields respective estimates for each of $L_o$ and $L_{air}$ by the fitting of each of the values of $d_N$ and $L_N$ of each of the first and second points in time to the model.

19. The method as recited in claim 1, wherein:

K represents the extinction coefficient;

M is a number of objects considered;

$L_o^m$ is a current estimate of intrinsic luminance of object m;

$L_{air}$ is a current estimate of air luminance;

$$S_{ed}^m \text{ is } \sum_{n=1}^{N_m} d_n^m e^{-Kd_n^m};$$

$N_m$ is a number of measurements for object m;

e is Euler's number;

$d_n^m$ is distance to object m for measurement n;

$$S_{ed} \text{ is } \sum_{m=1}^{M} S_{ed}^m;$$

$$S_{eed}^m \text{ is } \sum_{n=1}^{N_m} d_n^m e^{-Kd_n^m} e^{-Kd_n^m};$$

$$S_{eed} \text{ is } \sum_{m=1}^{M} S_{eed}^m;$$

$$S_{Led}^m \text{ is } \sum_{n=1}^{N_m} L_n^m d_n^m e^{-Kd_n^m};$$

$L_n^m$ is current estimate of luminance of object m for measurement n; and $$S_{Led} \text{ is } \sum_{m=1}^{M} S_{Led}^m;$$

20. The method as recited in claim 19, wherein the atmospheric extinction coefficient is determined by finding a value for the extinction coefficient in which $F(K)=0$.

21. The method as recited in claim 19, wherein:

$L_o^m$ is defined as $$\frac{S_{Le}^m + L_{air}(S_{ee}^m - S_e^m)}{S_{ee}^m};$$

$$S_{Le}^m \text{ is } \sum_{n=1}^{N_m} L_n^m e^{-Kd_n^m};$$

$$S_{ee}^m \text{ is } \sum_{n=1}^{N_m} e^{-Kd_n^m} e^{-Kd_n^m}; \text{ and}$$

$$S_e^m \text{ is } \sum_{n=1}^{N_m} e^{-Kd_n^m}.$$

22. The method as recited in claim 21, wherein:

$L_{air}$ is defined as $$\frac{S_L - \sum_{m=1}^{M} \frac{S_e^m S_{Le}^m}{S_{ee}^m}}{S_1 - \sum_{m=1}^{M} \frac{S_e^m S_e^m}{S_{ee}^m}};$$

$$S_L \text{ is } \sum_{m=1}^{M} S_L^m;$$

$$S_1 \text{ is } \sum_{m=1}^{M} S_1^m;$$

$$S_L^m \text{ is } \sum_{n=1}^{N_m} L_n^m; \text{ and}$$

$$S_1^m \text{ is } \sum_{n=1}^{N_m} 1.$$

23. The method as recited in claim 19, wherein:

$L_{air}$ is defined as $$\frac{S_L - \sum_{m=1}^{M} \frac{S_e^m S_{Le}^m}{S_{ee}^m}}{S_1 - \sum_{m=1}^{M} \frac{S_e^m S_e^m}{S_{ee}^m}};$$

$S_L$ is $\sum_{m=1}^{M} S_L^m$;

$S_1$ is $\sum_{m=1}^{M} S_1^m$;

$S_L^m$ is $\sum_{n=1}^{N_m} L_n^m$;

$S_1^m$ is $\sum_{n=1}^{N_m} 1$;

$S_{Le}^m$ is $\sum_{n=1}^{N_m} L_n^m e^{-K d_n^m}$;

$S_{ee}^m$ is $\sum_{n=1}^{N_m} e^{-K d_n^m} e^{-K d_n^m}$; and $S_e^m$ is $\sum_{n=1}^{N_m} e^{-K d_n^m}$.

24. The device as recited in claim 8, wherein:
K represents the extinction coefficient;
M is a number of objects considered;
$L_0^m$ is a current estimate of intrinsic luminance of object m;
$L_{air}$ is a current estimate of air luminance;

$S_{ed}^m$ is $\sum_{n=1}^{N_m} d_n^m e^{-K d_n^m}$;

$N_m$ is a number of measurements for object m;
e is Euler's number;
$d_n^m$ is distance to object m for measurement n;

$S_{ed}$ is $\sum_{m=1}^{M} S_{ed}^m$;

$S_{eed}^m$ is $\sum_{n=1}^{N_m} d_n^m e^{-K d_n^m} e^{-K d_n^m}$;

$S_{eed}$ is $\sum_{m=1}^{M} S_{eed}^m$;

$S_{Led}^m$ is $\sum_{n=1}^{N_m} L_n^m d_n^m e^{-K d_n^m}$;

$L_n^m$ is current estimate of luminance of object m for measurement n; and $S_{Led}$ is $\sum_{m=1}^{M} S_{Led}^m$;

25. The device as recited in claim 24, wherein the atmospheric extinction coefficient is determined by finding a value for the extinction coefficient in which F(K)=0.

26. The non-transitory machine-readable memory medium as recited in claim 9, wherein:
K represents the extinction coefficient;
M is a number of objects considered;
$L_0^m$ is a current estimate of intrinsic luminance of object m;
$L_{air}$ is a current estimate of air luminance;

$S_{ed}^m$ is $\sum_{n=1}^{N_m} d_n^m e^{-K d_n^m}$;

$N_m$ is a number of measurements for object m;
e is Euler's number;
$d_n^m$ is distance to object m for measurement n;

$S_{ed}$ is $\sum_{m=1}^{M} S_{ed}^m$;

$S_{eed}^m$ is $\sum_{n=1}^{N_m} d_n^m e^{-K d_n^m} e^{-K d_n^m}$;

$S_{eed}$ is $\sum_{m=1}^{M} S_{eed}^m$;

$S_{Led}^m$ is $\sum_{n=1}^{N_m} L_n^m d_n^m e^{-K d_n^m}$;

$L_n^m$ is current estimate of luminance of object m for measurement n; and $S_{Led}$ is $\sum_{m=1}^{M} S_{Led}^m$;

27. The non-transitory machine-readable memory medium as recited in claim 26, wherein the atmospheric extinction coefficient is determined by finding a value for the extinction coefficient in which F(K)=0.

* * * * *